United States Patent
Saulenas et al.

(10) Patent No.: US 8,882,711 B2
(45) Date of Patent: Nov. 11, 2014

(54) INSERTION DEVICE FOR A MEDICAL CONDUIT

(71) Applicants: William G. Saulenas, Wayne, NJ (US); Marion Gertraud Butz, Regensburg (DE); Mark DeStefano, Collegeville, PA (US); Matthew Clemente, Downingtown, PA (US)

(72) Inventors: William G. Saulenas, Wayne, NJ (US); Marion Gertraud Butz, Regensburg (DE); Mark DeStefano, Collegeville, PA (US); Matthew Clemente, Downingtown, PA (US)

(73) Assignee: Animas Corporation, West Chester, PA (US)

( * ) Notice: Subject to any disclaimer, the term of this patent is extended or adjusted under 35 U.S.C. 154(b) by 30 days.

(21) Appl. No.: 13/627,280

(22) Filed: Sep. 26, 2012

(65) Prior Publication Data

US 2013/0085449 A1    Apr. 4, 2013

Related U.S. Application Data

(60) Provisional application No. 61/541,124, filed on Sep. 30, 2011.

(51) Int. Cl.
*A61M 5/178*    (2006.01)
*A61M 5/158*    (2006.01)

(52) U.S. Cl.
CPC ....... *A61M 5/158* (2013.01); *A61M 2005/1585* (2013.01)
USPC .................................................. 604/164.01

(58) Field of Classification Search
USPC .............. 604/164.01–164.05, 164.09–164.12
See application file for complete search history.

(56) References Cited

U.S. PATENT DOCUMENTS

| | | | |
|---|---|---|---|
| 5,814,020 A * | 9/1998 | Gross | 604/141 |
| 2008/0281270 A1 | 11/2008 | Cross et al. | |
| 2010/0152666 A1 | 6/2010 | Carter et al. | |

FOREIGN PATENT DOCUMENTS

WO    WO 2012/108955 A2    8/2012

OTHER PUBLICATIONS

International Search Report, PCT application No. PCT/US2012/057914, European Patent Office, Rijswijk, Netherlands, Jan. 11, 2013, 4 pages.

* cited by examiner

*Primary Examiner* — Theodore Stigell

(57) ABSTRACT

The invention provides an insertion device for insertion of conduits into a body that, before and following deployment of the conduit into the body, has no components that require insertion into or removal from the device. Additionally, the device includes a component that not only prevents re-use or reopening of the device once it is activated, but also provides feedback to the user in the form of a resistance force to activation that must be overcome by the user to deploy the conduit.

10 Claims, 17 Drawing Sheets

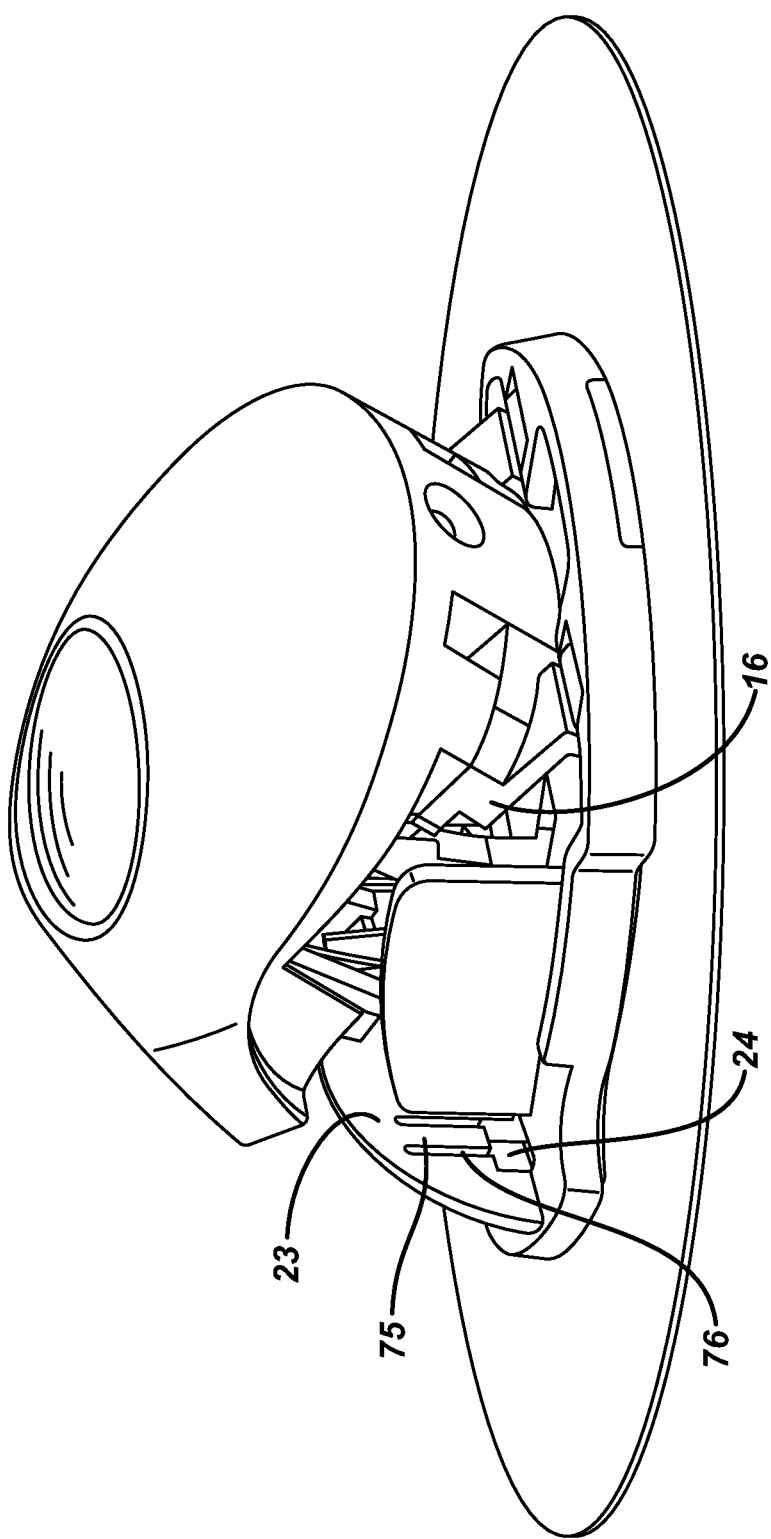

INSERTION DEVICE FOR A MEDICAL CONDUIT

RELATED APPLICATIONS

This application claims priority to U.S. Ser. No. 61/541,124 filed Sep. 30, 2011, which application is incorporated herein by reference.

FIELD OF THE INVENTION

The present invention relates, in general, to medical devices. In particular the invention relates to insertion devices useful in infusing substances into a body.

BACKGROUND OF THE INVENTION

Diabetes is a major health concern, because it can significantly impede the lifestyle of persons afflicted with this disease. Typically, treatment of the more severe form of the condition, Type I, or insulin-dependent diabetes, requires insulin to control glucose in the blood to prevent hyperglycemia that, if left uncorrected, can lead to ketosis. Hyperglycemia in diabetics also has been correlated with several long-term effects of diabetes, such as heart disease, blindness, hypertension, and kidney failure. Additionally, improper administration of insulin therapy can result in hypoglycemic episodes, that can cause coma and death.

Due to the debilitating effects resulting from abnormal blood glucose levels, insulin infusion pumps have been developed. These insulin delivery devices require that a reservoir of insulin be available to be delivered to the patient via a conduit that is a part of an infusion set. A variety of infusion sets employ conduits that permit access to body target sites in order to perform diagnostic, therapeutic, and surgical procedures, as well as to deliver insulin. For example, flexible cannulas inserted into a skin target site by rigid needles are conventionally employed for this purpose. There are several drawbacks in the use of infusion sets including the pain, discomfort, and anxiety associated with the deployment of the conduit under the patient's skin. It is therefore desirable to have an infusion set that is easy for the patient to use, that quickly and reliably inserts a fluid-carrying conduit to the appropriate depth under the skin, and that minimizes the anxiety associated with inserting the conduit.

BRIEF DESCRIPTION OF THE DRAWINGS

FIG. 13 is a rear perspective view of another embodiment of the device of the invention.

DETAILED DESCRIPTION OF THE INVENTION AND PREFERRED EMBODIMENTS

Figure 1:
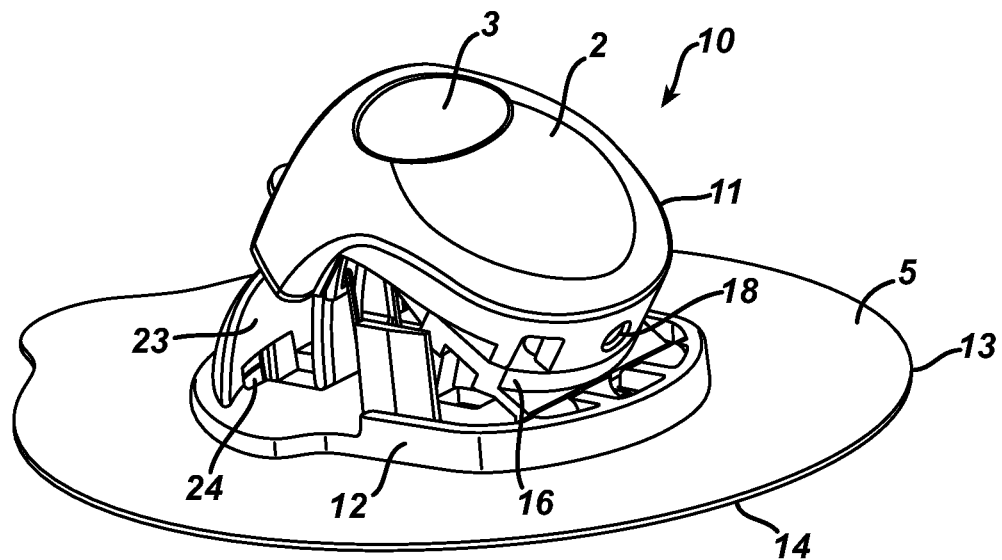
FIG. 1 is a rear perspective view of an embodiment of the device of the present invention.

The invention provides an insertion device for inserting conduits into a body for purposes of delivering fluids, drugs and the like through the conduit. The device of the invention likely will find its greatest utility in the insertion of conduits into subcutaneous tissues of the human body and still more utility in inserting flexible medical conduits into a body. The device is advantageous in that, before and following deployment of the conduit into the body, no components of the device, for example such as a needle, cannula protective cover or the like, need to be inserted or removed from the device. Additionally, the device includes a lock and force control component that not only prevents re-use or reopening of the device once it is activated, but also provides feedback to the user in the form of a resistance force to activation that must be overcome by the user to deploy the conduit. Because the force the user must apply to overcome the resistance force is greater than needed to deploy the conduit once activation occurs, full and quick deployment of the conduit is ensured. As yet another advantage, the device provides tactile feedback to the user to indicate when full conduit deployment, at which time the device locks, has occurred.

As shown in FIGS. 1 through 6, an insertion device 10 of the invention is provided having upper housing 11, guide 15, clamp 16, lower housing 12 and base 13. For purposes of the invention, the "top" of the device will refer to top surface 2 of upper housing 11 and the "bottom" refers to bottom surface 14 of base plate 13. "Proximal" means nearer to the top of the device than to the bottom and "distal" means nearer to the bottom than to the top.

Figure 7A:
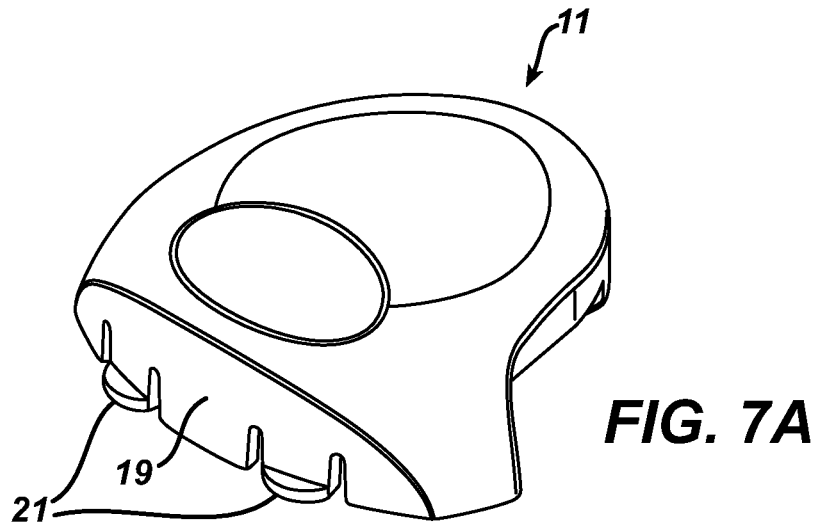
FIG. 7A is a top, front perspective view of the upper housing of the device of FIG. 1.
Figure 7B:
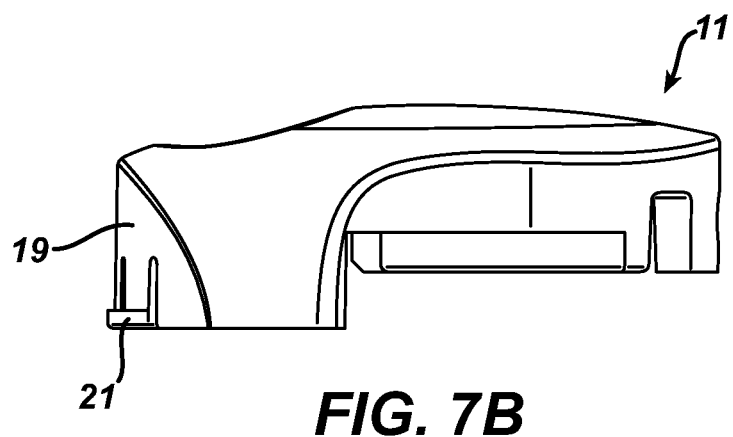
FIG. 7B is a side view of the upper housing of FIG. 7A.
Figure 7C:
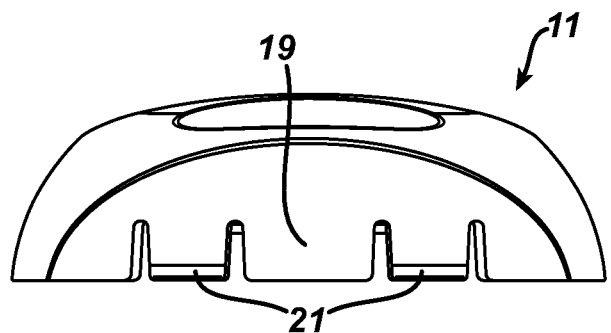
FIG. 7C is a front view of the upper housing of FIG. 7A.
Figure 7D:
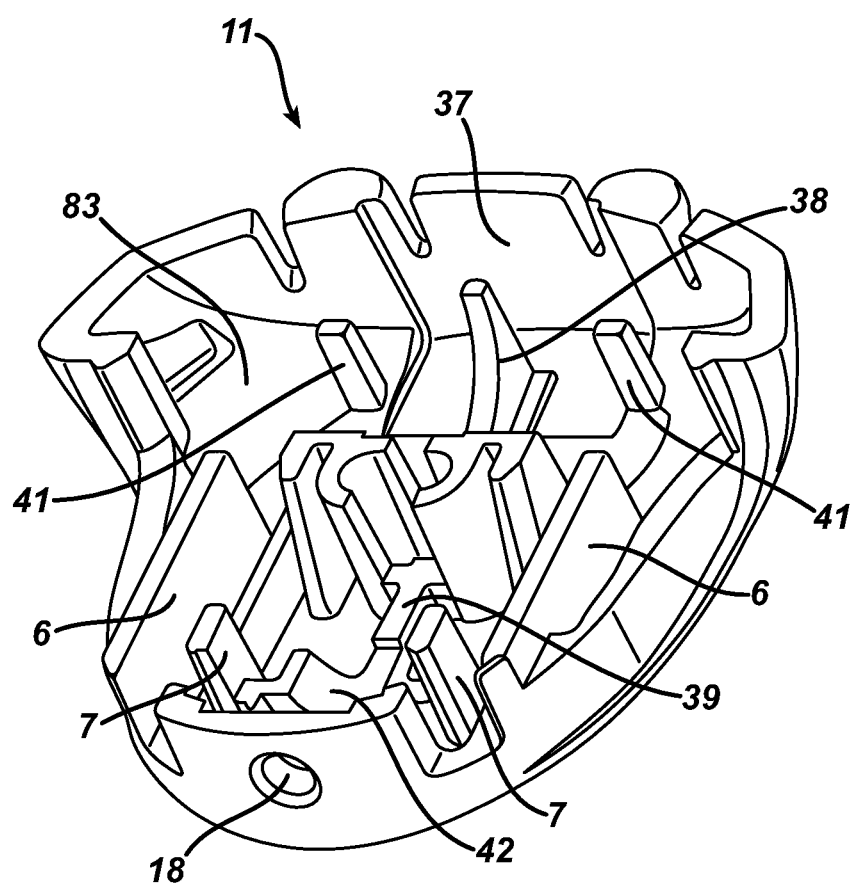
FIG. 7D is a bottom perspective view of the interior surface of the upper housing of FIG. 7A.
Figure 9A:
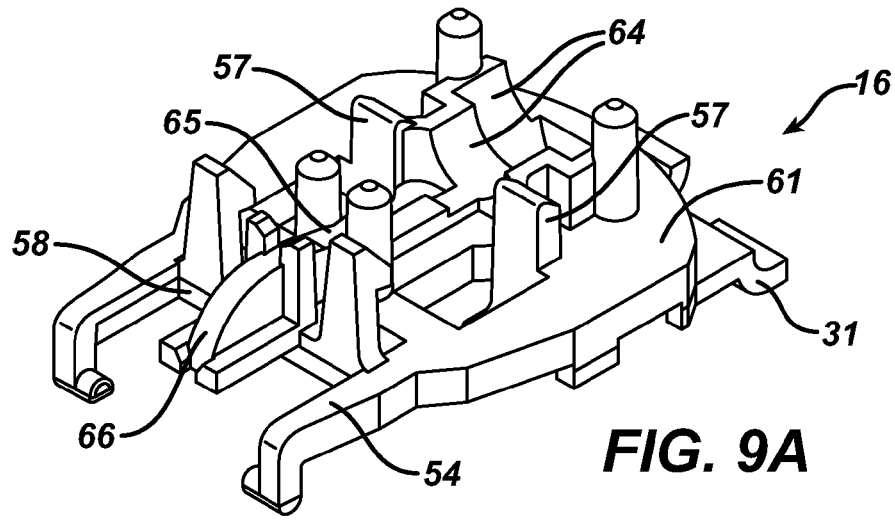
FIG. 9A is a top, front perspective view of an embodiment of the clamp component of the device of FIG. 1.
Figure 9B:
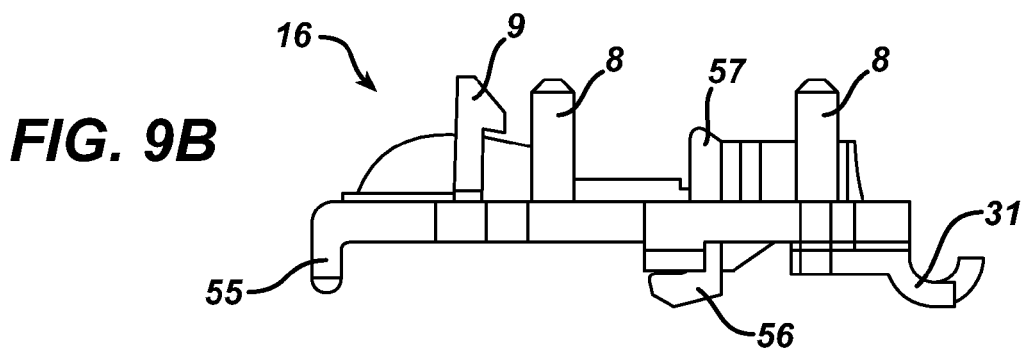
FIG. 9B is a side view of the clamp component embodiment of FIG. 9A.
Figure 9C:
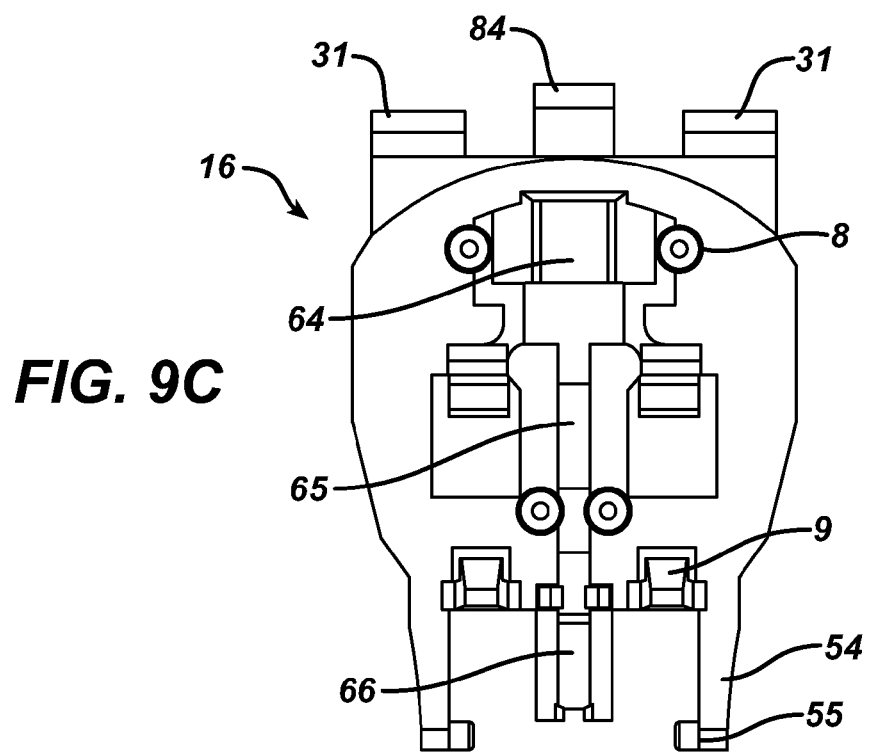
FIG. 9C is a top plan view of the clamp component embodiment of FIG. 9A
Figure 9D:
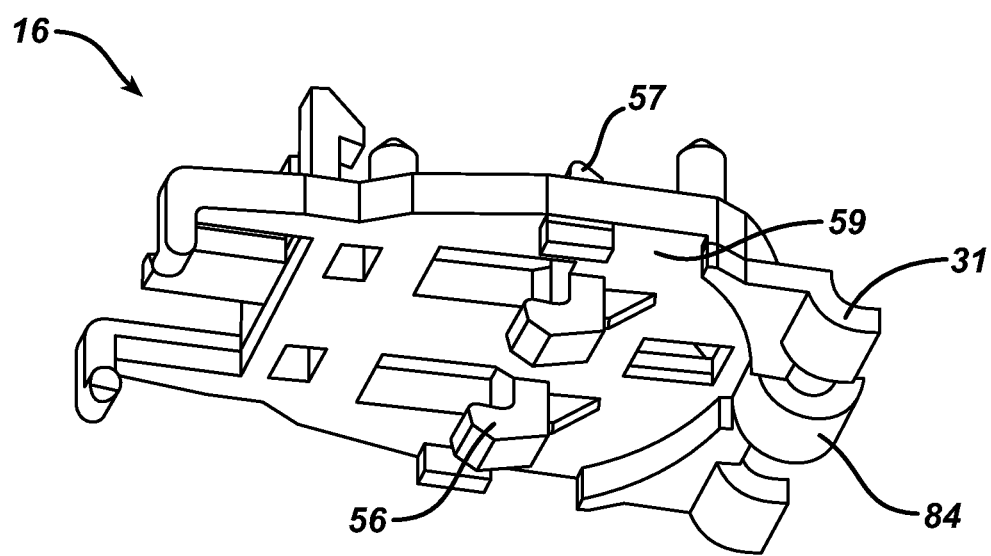
FIG. 9D is a bottom perspective view of the clamp component embodiment of FIG. 9A

As shown in FIG. 1, upper housing 11 may have one or more recesses 3 on top surface 2 to aid in user handling. Upper housing 11 is seated on the upper surface of clamp 16. Clamp 16 may be attached to upper housing 11 by adhesion, snap fit, welding, or the like. Alternatively, but less preferred, the upper housing and clamp may be a unitary component. Optionally, clamp 16 may include one or more posts 8 for insertion into recesses in the inside surface of upper housing 11 alone or in combination with one or more optional latch arms 9, as shown in FIG. 9B, to hold these components together. As still another option, extending downwardly from the internal surface of upper housing 11 may be post 7, as seen in FIG. 7D, which posts can be used to bond the clamp and upper housing together. Also to be noted in regards to the features of upper housing 11, and as shown in FIG. 7D, is optional upper housing side wall 6 which, along with lower housing side walls 4, shown in FIG. 10A, may provide a guide for insertion of a line-set connector into the device.

Figure 10A:
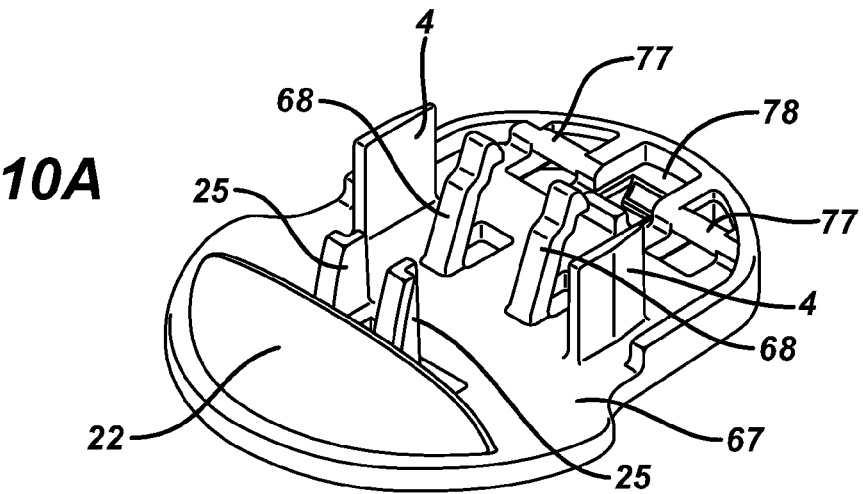
FIG. 10A is a front perspective view of the lower housing component of the device of FIG. 1.
Figure 10B:
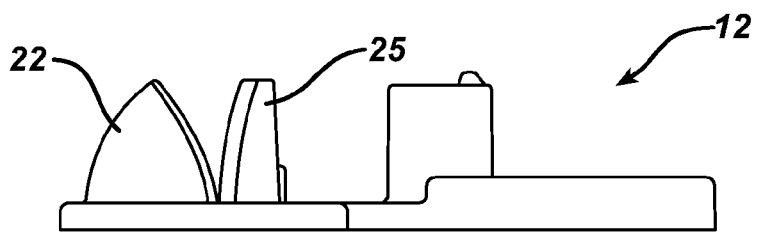
FIG. 10B is a side view of the lower housing of FIG. 10A.
Figure 10C:
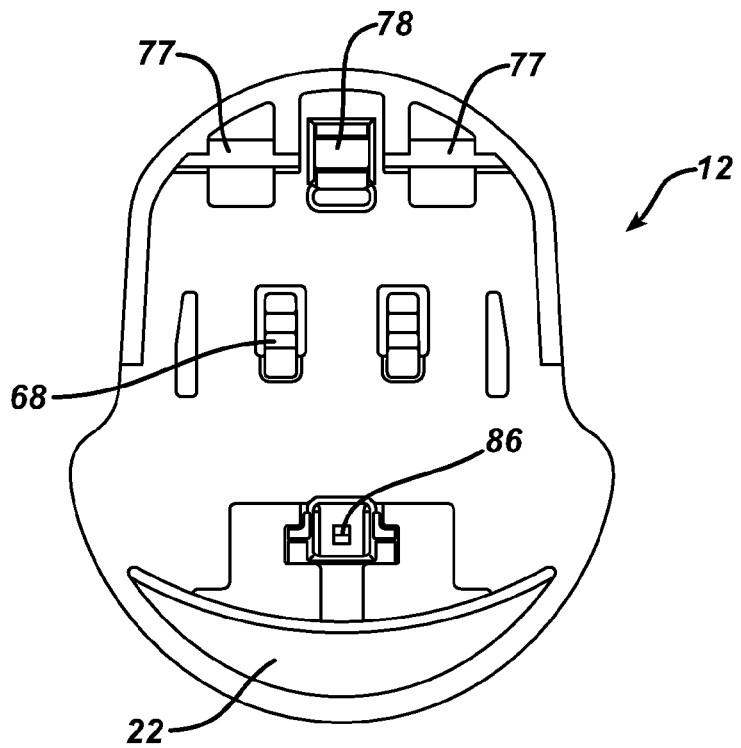
FIG. 10C is a top plan view of the lower housing of FIG. 10A

Clamp 16 may be attached by any convenient manner to lower housing 12 provided that the attachment is a movable attachment, meaning that clamp 16 is attached so that it is able to move, along with upper housing 11, upwardly and downwardly relative to lower housing 12 and permit closure of upper housing 11 and clamp 16 on lower housing 12. Preferably, clamp 16 is pivotably or hingedly attached to lower housing 12 to permit the upper housing and clamp to open and close in a "clam shell" manner relative to the bottom housing. As shown, clamp 16 is hingedly attached to lower housing 12 via one or more hinge pins 77. Hinge pins 77, as seen in FIGS. 10A through 10C, are located on at least one side, or preferably two opposite sides, of lower housing 12. As shown, hinge pins 77 lay within, and articulate with, a complementarily curved portion 31 of clamp 16. Optionally, clamp 16 includes tab 84 that is sized and shaped to fit into and rotate within groove 78 of lower housing 12 to aid in stabilizing the clamp and lower housing in relation to each other during closing of the device.

Lower housing 12 is disposed on top surface 5 of base plate 13. Preferably, base plate 13 is an adhesive patch or pad that attaches to the skin of the subject or patient. Alternatively, base plate 13 may be a semi-rigid or flexible plate the skin-facing surface, or bottom surface 14, of which is coated with an adhesive or has an adhesive pad attached thereto.

Figure 2:
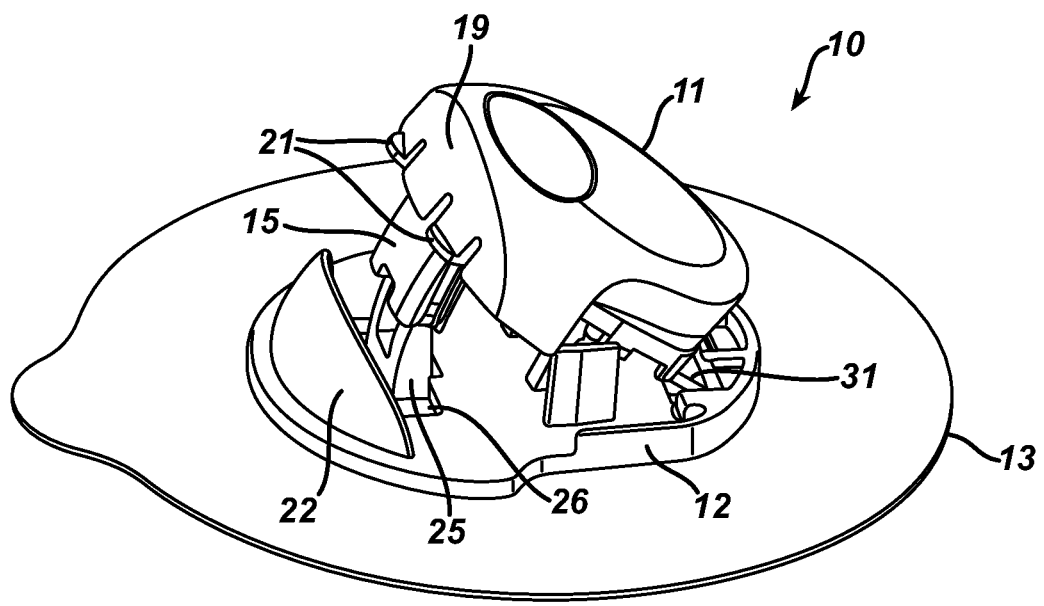
FIG. 2 is a top, front perspective view of the device of FIG. 1.
Figure 3:
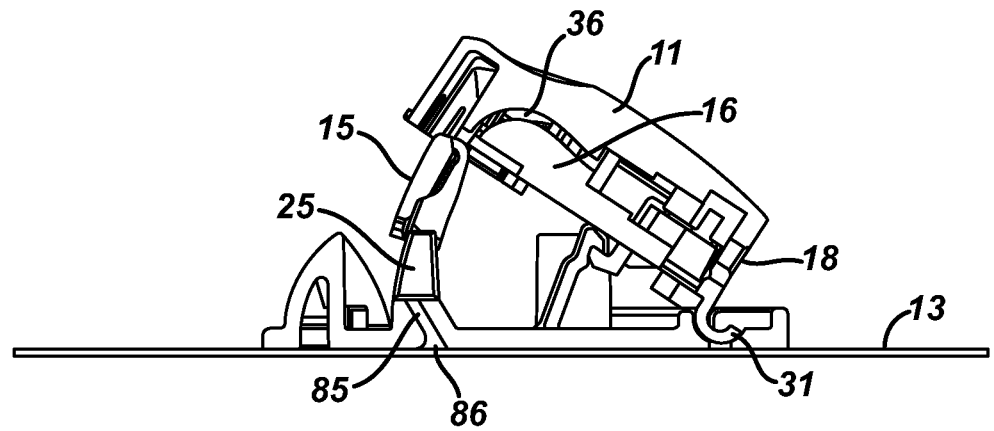
FIG. 3 is a cross-section view of the device of FIG. 1 in the open position without a conduit.
Figure 4:
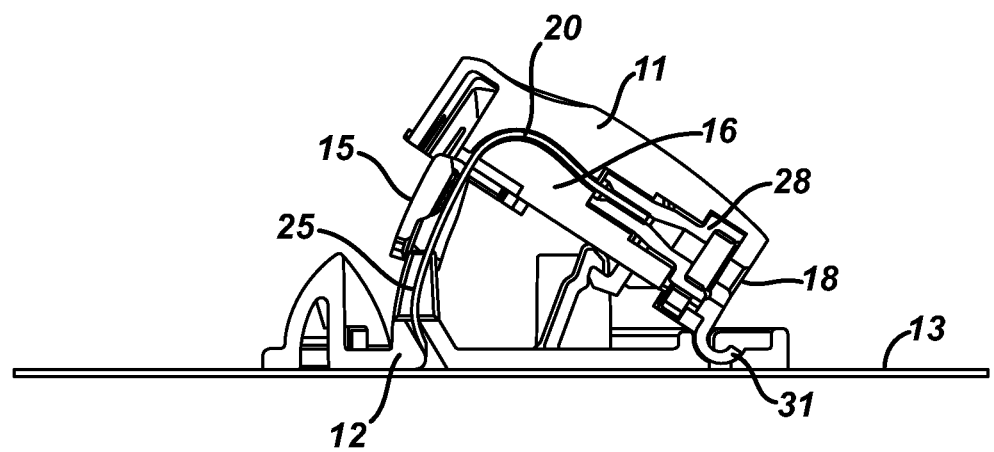
FIG. 4 is a cross-section view of the device of FIG. 1 in the open position with a conduit.
Figure 8A:
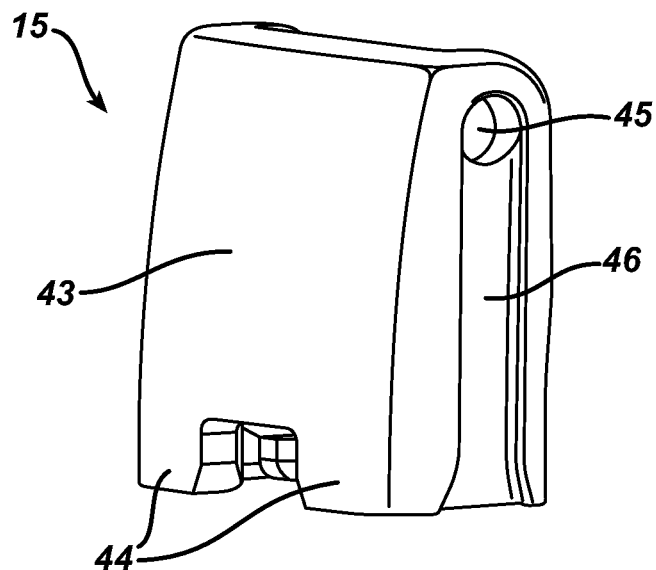
FIG. 8A is a front perspective view of the guide component of the device of FIG. 1.
Figure 8B:
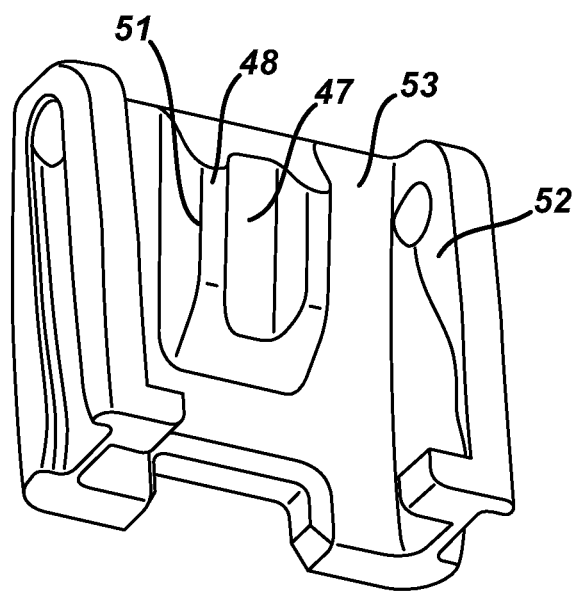
FIG. 8B is a bottom perspective view of the guide component of FIG. 8A.

The device of the invention preferably includes a guide for supporting of the conduit when the device is in the open, unactivated state. The guide may be of any suitable size and shape and, as shown in FIGS. 8A and 8B, guide 15 is an elongated "U-shaped" component. With reference to FIG. 7D, in upper housing 11 is found interior front surface 37, upper housing posts 41 and upper housing conduit support 39 that form an area that is of a complementary size and shape to guide 15 so that guide 15 fits substantially wholly within this area when the device is in its fully deployed and closed state. Clamp pins 55 of clamp 16 insert in holes 45 on either side of guide 15. At its distal end, the guide 15 is supported on the lower housing when the device is in its open, unactivated states. For example, guide 15 may include one or more support components, such as guide legs 44, that seat on or are supported by the lower housing, as for example by guide posts 25, when device 10 is in its open position as shown in FIGS. 2 through 4. In FIG. 8B is shown the internal surface of guide 15 which includes center support 48 on either side of which are internal guide channels, which channels are bounded by side wall internal surface 52, internal front surface 53 and center support outer surface 51. Center support 48 of guide 15 includes a conduit support component, which as shown is curved inner channel 47, that provides a path for and support for the portion of the conduit resting in the guide when the device is in its open, unactivated state and those portions passing through the guide as the device moves from its activated to its closed state. As device 10 is closed, upper housing posts 41 slide downwardly along recesses 46 on either side of guide 15 and upper housing 11 moves downwardly toward lower housing 12. At the same time, guide 15 and guide legs 44 move downwardly over lower housing posts 25.

Guide 15 may be coated so as to reduce the friction between it and the housing and conduit portions with which it articulates for example, by coating with a silicone lubricant oil. However, preferably, the guide is made of a lubricious polymer to facilitate friction reduction. Suitable lubricious polymers are well known in the art. Preferably, the lubricious polymer is polyoxymethyelene.

Figure 5:
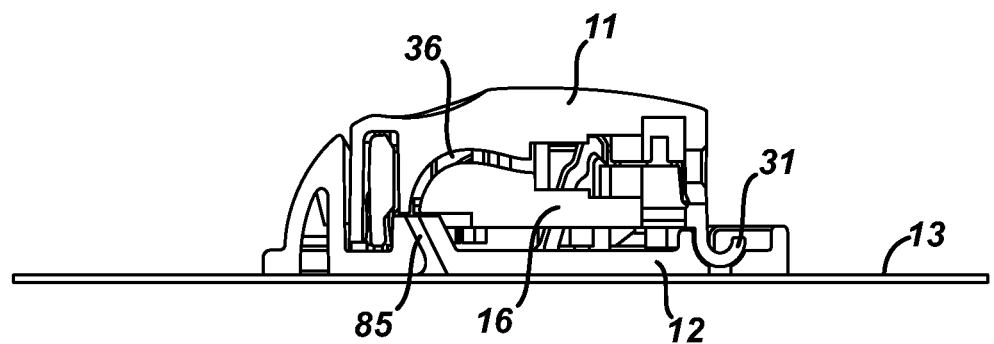
FIG. 5 is a cross-section view of the device of FIG. 1 in the closed position without a conduit.
Figure 6:
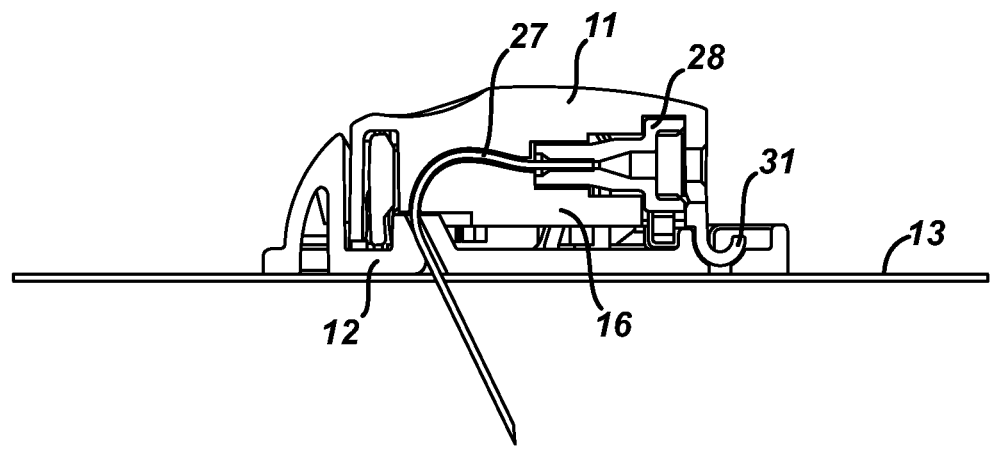
FIG. 6 is a cross-section view of the device of FIG. 1 in the closed position with a conduit.

With reference to FIGS. 10A through 10C, guide posts 25 arise upwardly from and are integral with interior surface 67 of lower housing 12 either individually or as a single unit. Upper housing 11, guide 15 and lower housing 12 are all sized and shaped so that, as upper housing 11 moves toward lower housing 12 upon activation of the device, these portions collapse in a reverse telescoping fashion. With reference to FIGS. 3 and 5, lower housing channel 85 is shown, which channel is formed within the lower housing and is preferably centered between guide posts 25. The lower housing channel communicates with a second channel located within the proximal portion of the device. The conduit is housed within the two channels and, upon activation of the device and deployment of the conduit, the conduit's distal portion moves through the lower housing channel and exits lower housing aperture 86.

With reference to FIGS. 9A through 9D, 11, 11A and 12A through E, device 10 incorporates a combined force control component. The force control component additionally provides a lock for the device once the conduit is deployed and the device is closed. The force control component, thus, is composed of at least one first part that releasably engages with the lower housing latch and at least one second part that non-releasably engages with the lower housing latch. As shown, the force control mechanism is composed of clamp 16 and latch 68 and clamp 16 includes "L" shaped clamp actuator 56 fixedly attached or integral with and extending from bottom surface 59 of clamp 16. Extending upwardly from top surface 61 of clamp 16 and preferably located opposite actuator 56 is clamp strike 57 which also may be fixedly attached or integral with clamp 16. One or more clamp arms 54 extend outwardly from front surface 58 and have "L" shaped clamp pins 55 extending downwardly therefrom. Clamp pins 55 enter lower housing openings 26, shown in FIG. 1, when the device is in its fully deployed and closed state.

Clamp 16 also includes clamp seat 64, integrally formed and arising from top surface 61, which holds the proximal end of a conduit. Clamp seat 64 may be of any size and shape suitable to securely hold the proximal portion of the conduit. Extending forwardly from and integral with clamp seat 64 is support body 65 that extends to and is integral with curved portion 66. With reference to FIG. 7D, arising from the interior surface of upper housing 11 is upper housing curved seat 42 that, when the upper housing is seated on the clamp, overlies clamp seat 64 and completes the enclosure for the conduit proximal end. Upper housing conduit support 39 extends forwardly from and is integral with upper housing seat 42 and is complementarily curved to section 66 at its forward-most portion 38. Channel 36, shown in FIGS. 3 and 5, for the body of the conduit is formed by components 65 and 66 of clamp 16 and components 38 and 39 of upper housing 11.

In regards to the force control component of device, clamp actuator 56 of clamp 16 releasably engages with latch 68 of lower housing 12, while clamp strike 57 non-releasably engages with latch 68. Device 10 may have one, but preferably has at least two latches 68 and at least two clamp actuators 56 to interact therewith. When more than one latch 68 is used, preferably, the latches are equally spaced apart from each other. Latch 68 is preferably integral with and arises from the inner surface 67 of lower housing 12. Latch 68 is composed of latch arm 69 at the proximal end of which arises detent lobe 71 and detent peak 72. Between detent lobe 71 and detent peak 72 is formed recess 74 sized and shaped to capture the distal-most end 73 of clamp actuator 56. The size and shape of recess 74 is slightly smaller than that required for a "hand-in-glove" fit for distal end 73 in recess 74, but sufficient for holding of distal end 73 at least partially within recess 74 so that a force is required to be exerted by the user to move distal end 73 out of recess 74.

Figure 11:
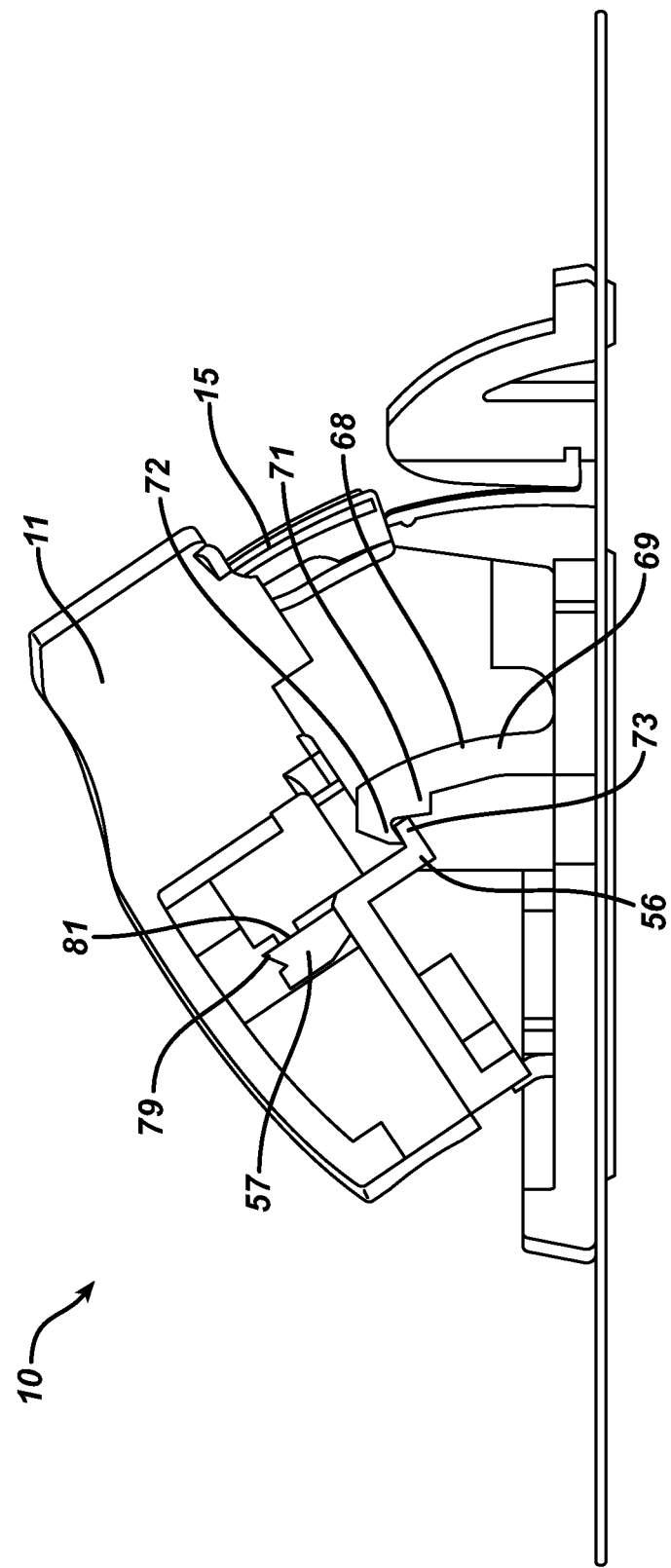
FIG. 11 is a side view of the device of FIG. 1 with a portion of the upper housing cut away.
Figure 11A:
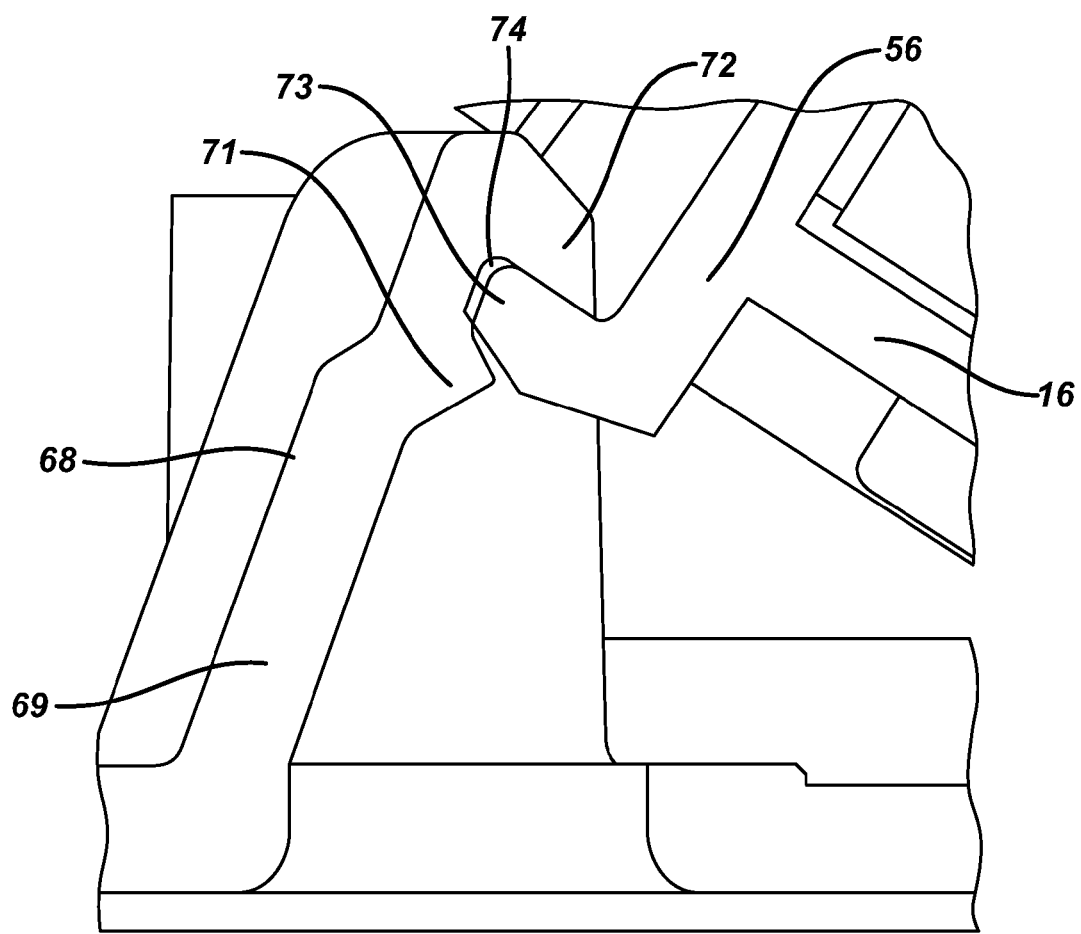
FIG. 11A is a magnified view of a portion of FIG. 7.

In use, device 10 is delivered to the user in the open, non-deployed state as shown, for example, in FIG. 4. In the non-deployed state, medical conduit 20 is fully retracted within the device and its sharp end is not exposed. In the non-deployed position, the end 73 of clamp actuator 56 rests in recess 74 as shown in FIG. 11A. The user places bottom surface 14 of base plate 13 against the target site and presses downwardly on upper housing 11 so that it moves lower housing 12 as shown in FIGS. 12A through E.

Figure 12A:
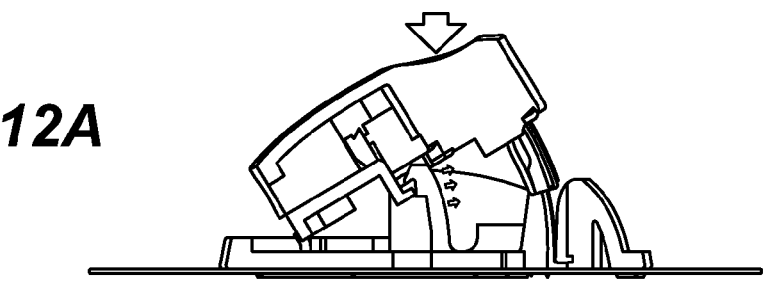
FIG. 12A shows the device of FIG. 7 as device activation is initiated.
Figure 12B:
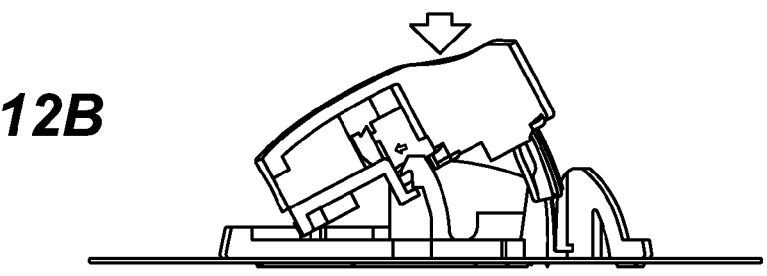
FIG. 12B shows the device of FIG. 7 as the device is in mid-closure.
Figure 12C:
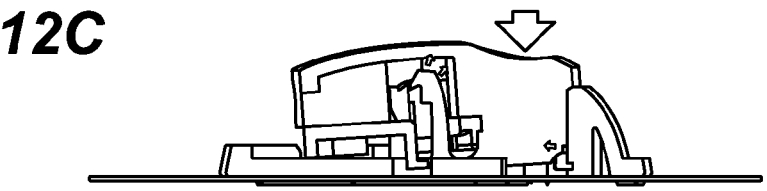
FIG. 12C shows the device of FIG. 7 at the initiation of locking latch engagement.
Figure 12D:
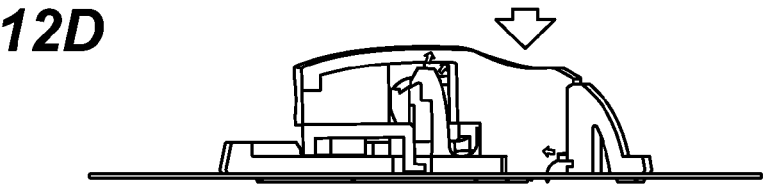
FIG. 12D is shows the continuation of device locking latch engagement
Figure 12E:
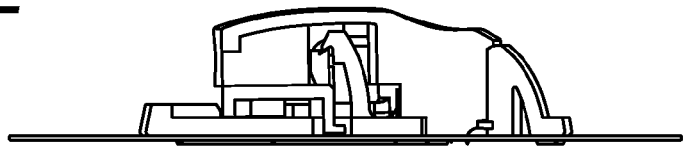
FIG. 12E shows the device in the closed, fully locked, and deployed position.

With reference to FIGS. 12A through 12E, as sufficient force is applied to upper housing 11, the device is activated and end 73 of clamp actuator 56 begins moving downwardly and engaging detent lobe 71 exerting pressure thereon and deflecting latch 68 forwardly, as indicated by the small arrows in FIG. 12A, and allowing for passage of end 73 of clamp actuator 56. The resistance force generated by the engagement of end 73 and detent lobe 71 is felt by the user and provides a key feedback to the user of the force required to activate the device and deploy the conduit, which force, due to the increased force required for the clamp actuator end to pass over the detent lobe ensures sufficient force for full deployment and quick insertion of the medical conduit. Once end 73 passes beyond detent lobe 71, the force required to continue the downward movement of upper housing 11 is markedly diminished.

As device activation continues, upper housing 11 continues its downward travel and prior to reaching the fully closed position, detent peak 72 will begin to engage front surface 81 of clamp peak 79 on clamp strike 57 again creating resistance. The force required to be applied to overcome this resistance results in deflection of latch arm 68 forwardly by peak 72. The user will detect the resistance generated by the interaction of detent peak 72 and front surface 81 which will serve as an indication to the user that full closure and locking of the device is imminent. Once clamp strike peak 79 moves sufficiently downwardly so that detent peak 72 is captured on strike peak 79, this serves to lock device 10 preventing upper housing 11 from being moved upwardly away from lower housing 12 on closing of the device.

One ordinarily skilled in the art will recognize that any of a wide variety of combined force control-lock components may achieve the same result as the disclosed clamp and latch. Examples of additional suitable components are shown in FIGS. 15 through 17.

An optional and preferred additional lock for the device is shown in FIGS. 1, 2, and FIGS. 7A through 7C. Front surface 19 of upper housing 11 has one or more latch tabs 21 projecting outwardly therefrom. Preferably two tabs 21, spaced equidistant from the side of front surface 19 are used. Tabs 21 may be of any convenient size and shape. On activation of device 10, upper housing 11 moves downwardly and tabs 21 contact the inside surface 23 of front plate 22 of lower housing 12 resulting in frictional resistance to closure of the housings. As the frictional resistance is overcome by the downward force on upper housing 11 applied by the user, tabs 21 travel along inside surface 23 until they encounter and enter tab slots 24. When this occurs, the device "snaps" closed and cannot be reopened providing a second lock for the device.

An alternative embodiment for the additional lock is shown in FIG. 13. In this embodiment, inside surface 23 of front plate 22 of lower housing 12 has flexible tab member 75 which extends outwardly and downwardly from the inside surface 23 and is movably attached thereto. Flexible tab member 75 may, and preferably does, additionally have slotted reliefs 76 on either side thereof, which provides a shaped path to slidably receive tab latch tab 21 therein. As upper housing 11 is moved downwardly toward and engages with lower housing 12, tab 21 engages with flexible tab member 75 moving it toward the front of lower housing 12. As upper housing 11 reaches its fully seated position on lower housing 12, tab 21 travels past the lower end of flexible tab member 75 and into tab slot 24 which is a slot formed within inside surface 56. As yet another alternative, the tab member may include a ramped portion.

Any conduit suitable for use in the device of the invention may be used, such as a needle, cannula, and a combination thereof. Additionally, the conduits used according to various embodiments of the present invention may include an elongated framework with a channel therethrough along a longitudinal axis thereof, which framework may be formed from a flexible material. Yet another alternative is to provide an elongated framework of a material that is then coated with a second material to form a channel.

Figure 14:
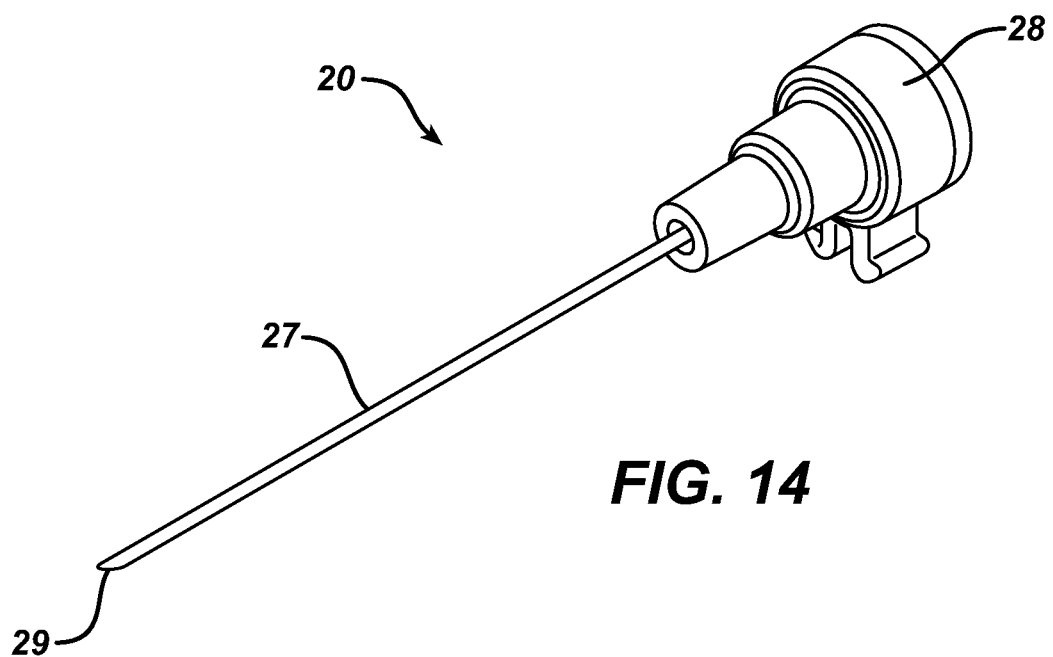
FIG. 14 is a front perspective view of a flexible medical conduit useful in the device of the invention.
Figure 14A:
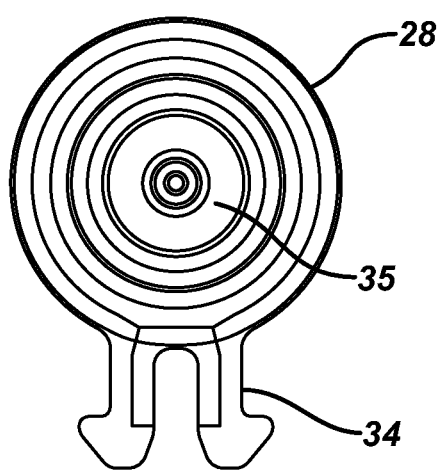
FIG. 14A is a end-on view of the proximal end of the conduit of FIG. 14.
Figure 15A:
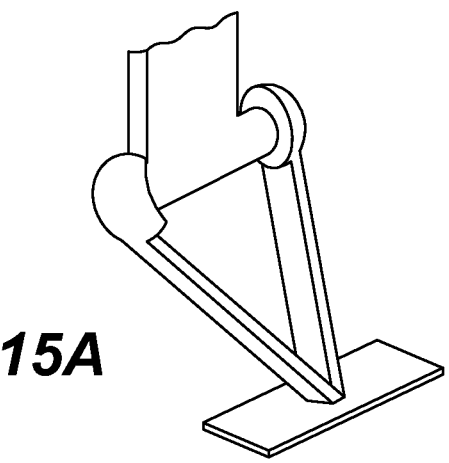
FIG. 15A is a perspective view of an alternative embodiment of a force control and locking component useful in the device of the invention.
Figure 15B:
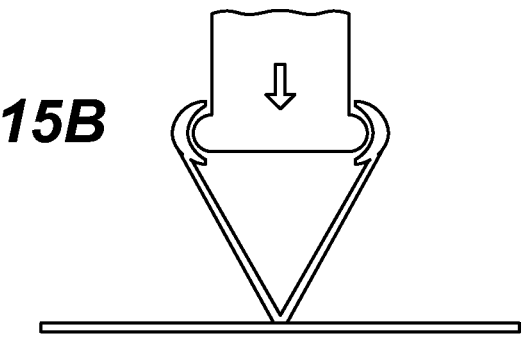
FIG. 15B is a front view of the component of FIG. 15A.
Figure 15C:
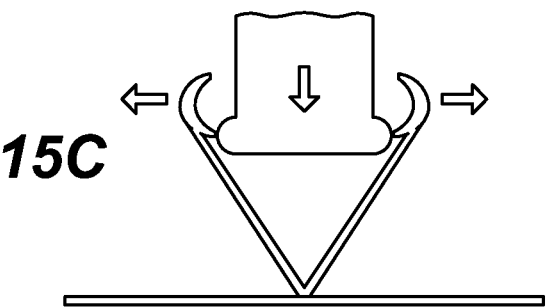
FIG. 15C is a front view of the component of FIG. 15A upon activation.
Figure 15D:
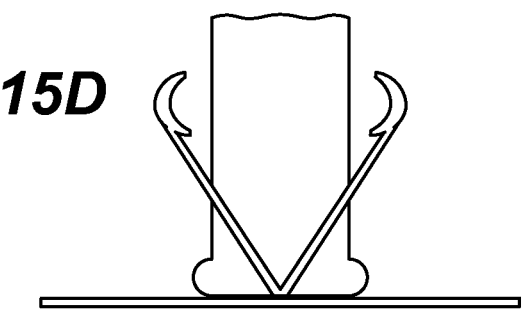
FIG. 15D is a front view of the component of FIG. 15A at device closure.
Figure 16A:
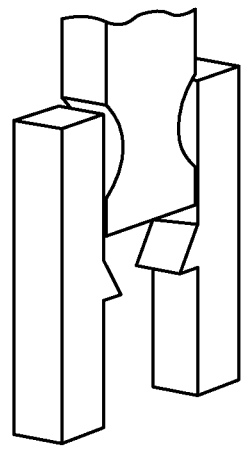
FIG. 16A is a perspective view of yet another alternative embodiment of a force control and locking component useful in the device of the invention.
Figure 16B:
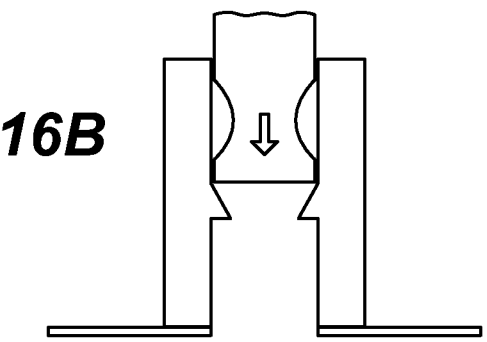
FIG. 16B is a front view of the component of FIG. 16A.
Figure 16C:
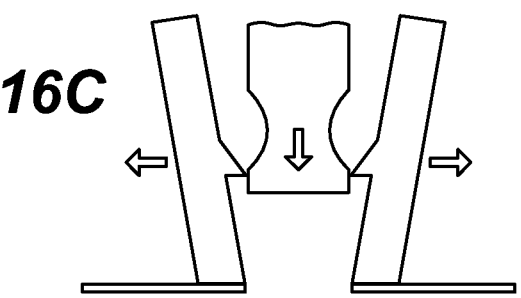
FIG. 16C is a front view of the component of FIG. 16A upon activation.
Figure 16D:
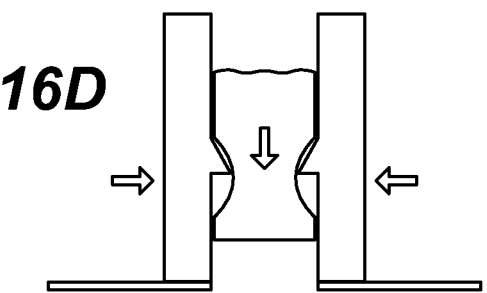
FIG. 16D is a front view of the component of FIG. 16A at device closure.
Figure 17A:
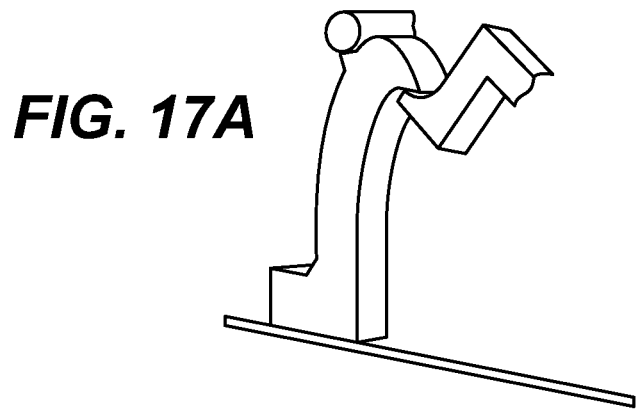
FIG. 17A is a perspective view of still another alternative embodiment of a force control and locking component useful in the device of the invention.
Figure 17B:
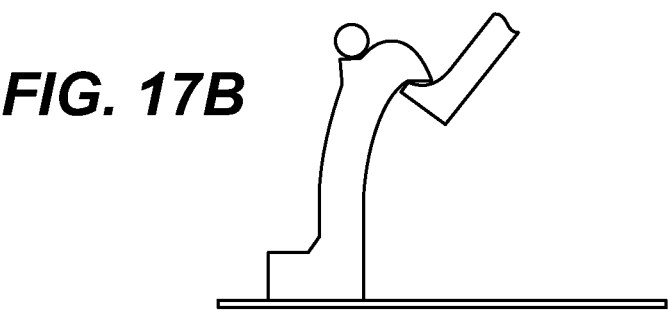
FIG. 17B is a front view of the component of FIG. 17A.
Figure 17C:
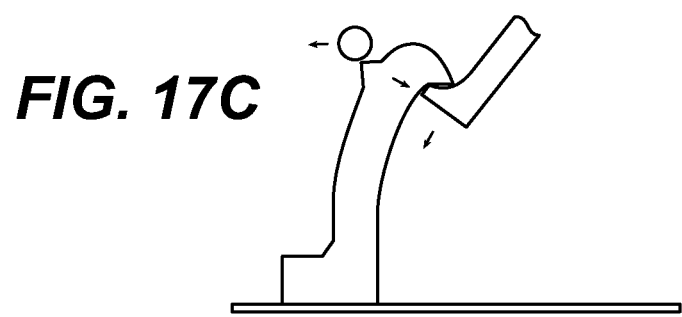
FIG. 17C is a front view of the component of FIG. 17A upon activation.
Figure 17D:
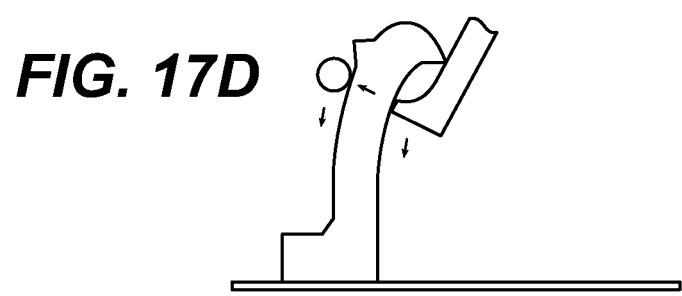
FIG. 17D is a front view of the component of FIG. 17A at device closure.

Shown in FIG. 14 is a preferred conduit 20, which is a conduit useful in the device of the invention. More preferably, conduit 20 is a flexible medical conduit. Such conduits typically have an elongated body portion 27, pointed or sharpened distal end 29 and proximal end 28. The body 27 of the flexible medical conduit is made from material that is compatible with use in the dermal and subcutaneous tissues of the body and has a modulus of elasticity that permits the gauge of the conduit to be small, meaning about 30 gauge or smaller. Additionally, the material preferably is such that it is kink-resistant and can remain in a curved or bent position during storage, yet allows for at least a portion of the conduit to regain a substantially straight shape when fully deployed from the device of the invention. Examples of suitable materials for the body of the flexible medical conduits useful in the device of the invention include nitinol, polyethylene ether ketone, polytetrafluoroethylene, aluminum, titanium and combinations thereof. Preferably, nitinol is used. Nitinol employed in embodiments of the present invention can be beneficially pre-processed, or pre-programmed, using techniques known to one skilled in the art to possess a variety of superelastic characteristics that are also known to those of skill in the art such as, for example, kink-resistance, the ability to accommodate large loads and the ability to return to an original shape following release of mechanically deforming stresses. Flexible medical conduits useful in the invention are available from the Nitinol Devices and Components Corporation.

As shown, flexible medical conduit 20 has proximal end 28 configured to provide a fluid-tight connection to associated medical device components such as the infusion components of a medication pump. As shown, proximal end 28 includes pierceable septum 35. Optionally, and as shown, proximal end 28 may include prongs 34 extending downwardly therefrom sized and shaped to aid securing of the proximal end 28 into the clamp seat 64. Flexible medical conduit may be coated with a suitable lubricious coating to aid in its movement within the device.

Flexible medical conduits useful in the present invention are beneficial in that, for example, they can be consistently inserted to a predetermined depth below the skin, are comfortably flexible while being kink-resistant, and have a relatively small cross-sectional area. For example, a typical catheter used in known infusion sets is about 584 microns in diameter and the conduits useful in the invention preferably are about three-quarters or less of that typical diameter. The kink-resistance enables the use of a flexible tube with a relatively a thin wall, meaning equal to or less than about 50 microns. Additionally, the flexible medical conduits can conform to and travel through the curved channel of the preferred embodiments of the device of the invention.

As shown in FIGS. 3 and 4, a channel 36 is formed by upper housing 11 and clamp 16. Proximal end 28 of conduit 20 is held within the area formed by clamp seat 64 and curved seat 42 while body 27 of conduit 20 extends through channel 36. In the device's open, unactivated state, at least a portion of conduit body 27 is supported by curved channel 47 of guide 15 and the distal-most end 29 of the conduit lies in channel 85 formed within lower housing 12. When the device is fully deployed and closed, the portion of conduit body 27 remaining within the device resides in channels 36 and 85.

The internal dimensions of the channels within the device are such that conduit 20 passes therethrough with minimal friction being generated. Optionally, the internal surface of the channels may be coated with a suitable lubricious coating or made from a lubricious material to facilitate passage of medical conduit 20 and minimize friction.

Opening 18 in upper housing 11 provides access to proximal end 28 of conduit 20 for purposes of connecting the conduit to a medication infusion pump. The connection may be made via any desired mechanism, but preferably is a fluid-tight connection.

One ordinarily skilled in the art will recognize that the device may be constructed to require a wide variety of force application to activate the device. Preferably, the device is designed to require that the user apply about 5 N to about 15 N of force to activate the device. The geometric dimensions of the various interacting parts of the latch and clamp, the materials selected for constructing these components, as well as the dimensions, materials of construction, and channel for the conduit all will determine the force necessary for activation and deployment of the device. It is within the skill of one of ordinary skill in the art to balance these factors to achieve the results of this invention The materials selected for use in the device preferably are polypropylene or a butadiene styrene including acrylonitrile butadiene styrene and methyl methacrylate acrylonitrile butadiene styrene, and combinations thereof. Preferably, the material used for the clamp is more rigid than that used for the upper and lower housing and latch to facilitate the interaction of these components. More preferably, the material selected for the clamp is polypropylene and that used for the housings and latch is methyl methacrylate acrylonitrile butadiene.

One ordinarily skilled in the art will recognize that any of a wide variety of surface configurations may be used for the combination force control-lock component. Further, materials of construction, the widths and thickness can be varied to control the forces of the interacting components of the device. The shape and length of the path of travel of the components can be controlled to facilitate additional control over the required closure force. While the figures illustrate force control-lock components and additional locks being placed at certain location on and within the housings, variations of the cooperate relationship between the mechanical structures can be alternated between the upper and lower housing by those skilled in the art.

The latch-clamp alone or in combination with the additional locking features of the device avoid the possibility of the spread of germs or disease often associated with the re-use of medical insertion devices such as needles and syringes. Further, these locking features also produce an audible "click" when closure and locking occurs, confirming completion of conduit travel and, thus, insertion of the conduit into the patient.

What is claimed is:

1. An insertion device for inserting a conduit into a body, the device comprising:
   a base plate;
   a lower housing disposed on a first surface of the base plate, the lower housing comprising a latch, at least one guide support, and a first channel through the lower housing;
   a guide for supporting at least a portion of the conduit while the device is in an unactivated state, wherein the guide is movably engagable with the lower housing;
   a clamp movably attached to a first end of the lower housing, the clamp comprising at least one first component that releasably engages with the lower housing latch and a second component that non-releasably engages with the lower housing latch
   an upper housing seated on the clamp and movably engaged with the guide;
   a second channel in communication with the first channel; and
   wherein the conduit is housed within the first and second channels.

2. The insertion device of claim 1, wherein the at least one first component comprises at least one actuator extending from a first surface of the clamp and the at least one second component comprises at least one strike extending from a second surface of the clamp.

3. The insertion device of claim 2, wherein the clamp strike is located substantially opposite the clamp actuator.

4. The device of claim 1, wherein the second channel is formed between the clamp and the upper housing.

5. The device of claim 1, comprising at least one additional lock.

6. The insertion device of claim 5, wherein the at least one additional lock comprises at least one latch tab for frictionally engaging an inner surface of the lower housing on a front surface of the upper housing and at least one tab slot on the inner surface of the lower housing for non-releasable engagement of the at least one latch tab.

7. The insertion device of claim 6, wherein the lower housing inner surface further comprises at least one flexible tab member for frictional engagement with the at least one latch tab.

8. The insertion device of claim 7, wherein the lower housing inner surface further comprises at least one slotted relief.

9. The insertion device of claim 7, wherein the lower housing inner surface further comprises slotted reliefs on either side of the at least one flexible tab member.

10. The insertion device of claims 1, 2, or 5, wherein the conduit is a flexible medical conduit.

\* \* \* \* \*